(12) United States Patent
Wahl et al.

(10) Patent No.: US 12,685,529 B2
(45) Date of Patent: *Jul. 21, 2026

(54) SURGICAL STAPLE IMPLANT KIT

(71) Applicant: In2Bones USA, LLC, Memphis, TN (US)

(72) Inventors: Rebecca Hawkins Wahl, Escondido, CA (US); Alan G. Taylor, Memphis, TN (US); Casey M. Chambers, Memphis, TN (US)

(73) Assignee: In2Bones USA, LLC, Memphis, TN (US)

(*) Notice: Subject to any disclaimer, the term of this patent is extended or adjusted under 35 U.S.C. 154(b) by 757 days.

This patent is subject to a terminal disclaimer.

(21) Appl. No.: 17/410,587

(22) Filed: Aug. 24, 2021

(65) Prior Publication Data

US 2021/0378665 A1 Dec. 9, 2021

Related U.S. Application Data

(60) Continuation of application No. 16/377,836, filed on Apr. 8, 2019, now Pat. No. 11,103,240, which is a
(Continued)

(51) Int. Cl.
| | |
|---|---|
| *A61B 17/068* | (2006.01) |
| *A61B 17/10* | (2006.01) |
| *A61B 17/17* | (2006.01) |
| *A61B 50/33* | (2016.01) |
| *B65B 7/16* | (2006.01) |
(Continued)

(52) U.S. Cl.
CPC ........ *A61B 17/068* (2013.01); *A61B 17/0682* (2013.01); *A61B 17/10* (2013.01); *A61B 17/17* (2013.01); *A61B 50/33* (2016.02); *B65B 7/16*

(2013.01); *A61B 2017/0645* (2013.01); *A61B 2017/0688* (2013.01); *A61B 17/885* (2013.01); *A61B 50/30* (2016.02);
(Continued)

(58) Field of Classification Search
CPC .......................... A61B 17/068; A61B 17/0682
See application file for complete search history.

(56) References Cited

U.S. PATENT DOCUMENTS

| | | | | |
|---|---|---|---|---|
| 2013/0213843 A1* | 8/2013 | Knight | ............... | A61B 17/0642 |
| | | | | 206/438 |
| 2014/0097228 A1* | 4/2014 | Taylor | .................. | A61B 17/068 |
| | | | | 227/181.1 |
| 2016/0199060 A1* | 7/2016 | Morgan | ............... | A61B 17/068 |
| | | | | 227/175.1 |

* cited by examiner

*Primary Examiner* — Andrew Yang
(74) *Attorney, Agent, or Firm* — Rutan & Tucker LLP; Hani Z. Sayed

(57) ABSTRACT

An apparatus and a method are provided for a sterile staple implant kit that a surgeon may unpack and utilize during a surgery. The staple implant kit comprises a group of complementary surgery-specific instruments that are packaged in a sterile state. An instrument tray is configured to preserve the instruments in the sterile state until the staple implant kit is opened during the surgery. The instrument tray is configured to provide the surgeon with easy access to the instruments during the surgery. The staple implant kit comprises at least a staple inserter and a surgical staple suitable for being implanted in parallel holes drilled across a bone fusion or fixation site of a patient. The surgical staple preferably is loaded in a relaxed configuration into the staple inserter. A staple retention clip retains the surgical staple in the staple inserter until the staple is distracted during the surgery.

19 Claims, 7 Drawing Sheets

Related U.S. Application Data division of application No. 15/487,305, filed on Apr. 13, 2017, now Pat. No. 10,893,862.

(60) Provisional application No. 62/322,054, filed on Apr. 13, 2016.

(51) Int. Cl.

| | |
|---|---|
| *A61B 17/064* | (2006.01) |
| *A61B 17/88* | (2006.01) |
| *A61B 50/30* | (2016.01) |
| *A61B 90/00* | (2016.01) |
| *B65B 55/12* | (2006.01) |

(52) U.S. Cl.

CPC . *A61B 2090/061* (2016.02); *A61B 2090/0807* (2016.02); *B65B 55/12* (2013.01)

SURGICAL STAPLE IMPLANT KIT

PRIORITY

This application claims the benefit of and priority to U.S. patent application Ser. No. 16/377,836 filed on Apr. 8, 2019 and U.S. patent application filed on Apr. 13, 2017 and having application Ser. No. 15/487,305, now issued as U.S. Pat. No. 10,893,862 and U.S. Provisional application, entitled "Surgical Staple Implant Kit," filed on Apr. 13, 2016 and having application Ser. No. 62/322,054.

FIELD

The field of the present disclosure generally relates to securing bones together. More particularly, the field of the disclosure relates to an apparatus and a method for a sterile staple implant kit that a surgeon may unpack and utilize during bone fusion or fixation surgery.

BACKGROUND

Surgical staples or a fusion bone plate implant utilized in conjunction with one or more fasteners may be used to generate compression and stability at a bone interface. An implant generally serves to stabilize bones, or bone parts, relative to one another so as to promote bone fusion. In many applications, surgical staples, or bone plates and fasteners are used to fuse bones, or bone parts, of the human body, such as bones in the foot, the ankle, the hand, the wrist, as well as various other portions of the body. Surgical staples are particularly advantageous in the hands and feet due to a low dorsal profile of the staples once they are implanted. Furthermore, during the course of certain medical procedures, a surgeon may immobilize one or more bones or bone fragments by stabilizing the bones together in a configuration which approximates the natural anatomy. To this end, the surgeon may use fasteners to attach the bones to a bone plate implant so as to hold the bones in alignment with one another while they fuse together.

SUMMARY

An apparatus and a method are provided for a sterile staple implant kit that a surgeon may unpack and utilize during a surgery. The staple implant kit is comprised of a group of complementary surgery-specific instruments that are packaged in a sterile state. An instrument tray is configured to preserve the group of instruments in the sterile state until the staple implant kit is opened during the surgery. The instrument tray is configured to provide the surgeon with easy access to the group of instruments during the surgery. The staple implant kit comprises at least a staple inserter and a surgical staple suitable for being implanted in parallel holes drilled across a bone fusion or fixation site of a patient. The surgical staple preferably is loaded in a relaxed configuration into the staple inserter. A staple retention clip retains the surgical staple in the staple inserter until the staple is distracted during the surgery. In some embodiments, the group of instruments may be further comprised of any of various surgical tools, such as, for example, drill sizers, forceps, staple removal tools, temporary pins, drill depth stops, fusion bone plates, bone plate fasteners, compression screws, and the like.

In an exemplary embodiment, a sterile staple implant kit that a surgeon may unpack and utilize during a surgery comprises a staple inserter and a surgical staple; a group of complementary surgery-specific instruments that are packaged in a sterile state; and an instrument tray configured to preserve the instruments in the sterile state and provide easy access to the instruments during the surgery.

In another exemplary embodiment, the group of instruments comprises at least the staple inserter and the surgical staple, the surgical staple being loaded into the staple inserter in a relaxed configuration of the surgical staple. In another exemplary embodiment, the group of instruments comprises at least the staple inserter, the surgical staple, a bone drill, a drill guide, a locator pin, and a tamp. In another exemplary embodiment, the group of instruments further comprises any of various surgical tools, such as drill sizers, forceps, staple removal tools, temporary pins, drill depth stops, fusion bone plates, bone plate fasteners, compression screws, and the like.

In another exemplary embodiment, the staple inserter comprises a body supporting a distal force applicator that is mechanically coupled with a proximal handle, the distal forced applicator configured to distract the surgical staple when the proximal handle is rotated in a clockwise direction. In another exemplary embodiment, rotation of the proximal handle moves a driver relative to a crown of the surgical staple, such that clockwise rotation of the proximal handle clasps the crown between the driver and a pair of grips disposed within the distal force applicator, further clockwise rotation changing the surgical staple from a relaxed configuration to a distracted configuration suitable for implantation across a bone fusion or fixation site of a patient. In another exemplary embodiment, the pair of grips comprises a first grip and a second grip, the first grip being disposed near a first leg of the surgical staple, and the second grip being disposed near a second leg of the surgical staple, the first and second grips being configured to engage the crown on the same side of the surgical staple. In another exemplary embodiment, rotating the proximal handle counterclockwise allows the surgical staple to relax from being distracted. In another exemplary embodiment, a staple retention clip is coupled with the distal force application to retain the surgical staple in a relaxed state during sterilization, packaging, and shipping. In another exemplary embodiment, the staple retention clip is configured to be removed from the distal force applicator during or after distracting the surgical staple prior to being implanted into a bone of a patient.

In another exemplary embodiment, the group of instruments includes a drill guide comprising a proximal handle and a pair of parallel sleeves configured to direct drilling of parallel holes across a bone fusion or fixation site of a patient, the positions of the parallel sleeves being substantially similar to a distance between a first leg and second leg of the surgical staple in a distracted configuration. In another exemplary embodiment, each of the parallel sleeves is configured to receive and guide a bone drill configured for drilling holes in human bone. In another exemplary embodiment, the group of instruments comprises a locator pin configured to be inserted through a first sleeve of the drill guide into a newly drilled hole in the bone of the patient during drilling of a second hole in the bone by way of the second sleeve of the drill guide.

In an exemplary embodiment, a staple sizer for determining sizes of surgical staples during surgery comprises a disc-shaped member comprising a plurality of sections corresponding to different sizes of surgical staples; a pair of parallel protrusions disposed within each of the plurality of sections and extending away from the center of the staple sizer; and a pair of holes disposed adjacently to each pair of parallel protrusions.

In another exemplary embodiment, the parallel protrusions are configured to correspond to the positions of a first leg and a second leg of the surgical staple in a distracted state of the surgical staple. In another exemplary embodiment, each of the plurality of sections comprises a size indicator configured to display a size of the surgical stable that, when distracted, comprises first and second legs that substantially match the positions of the parallel protrusions. In another exemplary embodiment, the pair of holes are configured to indicate a relationship between holes in bone suitably drilled across a bone fusion or fixation site of a patient, the pair of holes corresponding to positions of a first leg and a second leg of the surgical staple in a distracted state of the surgical staple.

In an exemplary embodiment, a method for a sterile surgery-specific kit for use during performing a surgery comprises assembling a group of complementary instruments that are suitable for the surgery; sterilizing the group of complementary instruments; configuring an instrument tray suitable to preserve the group of complementary instruments in a sterile state, the instrument tray being configured to provide easy access to the group of complementary instruments during the surgery; packaging the group of complementary instruments in the sterile state into the instrument tray; and sealing the instrument tray to preserve the sterile state until the surgery-specific kit is opened during the surgery.

In another exemplary embodiment, assembling comprises including at least a staple inserter and a surgical staple in the group of complementary instruments. In another exemplary embodiment, assembling further comprises loading the surgical staple in a relaxed configuration into the staple inserter, a staple retention clip being configured to retain the surgical staple coupled with the staple inserter.

BRIEF DESCRIPTION OF THE DRAWINGS

The drawings refer to embodiments of the present disclosure in which.

Figure 1:
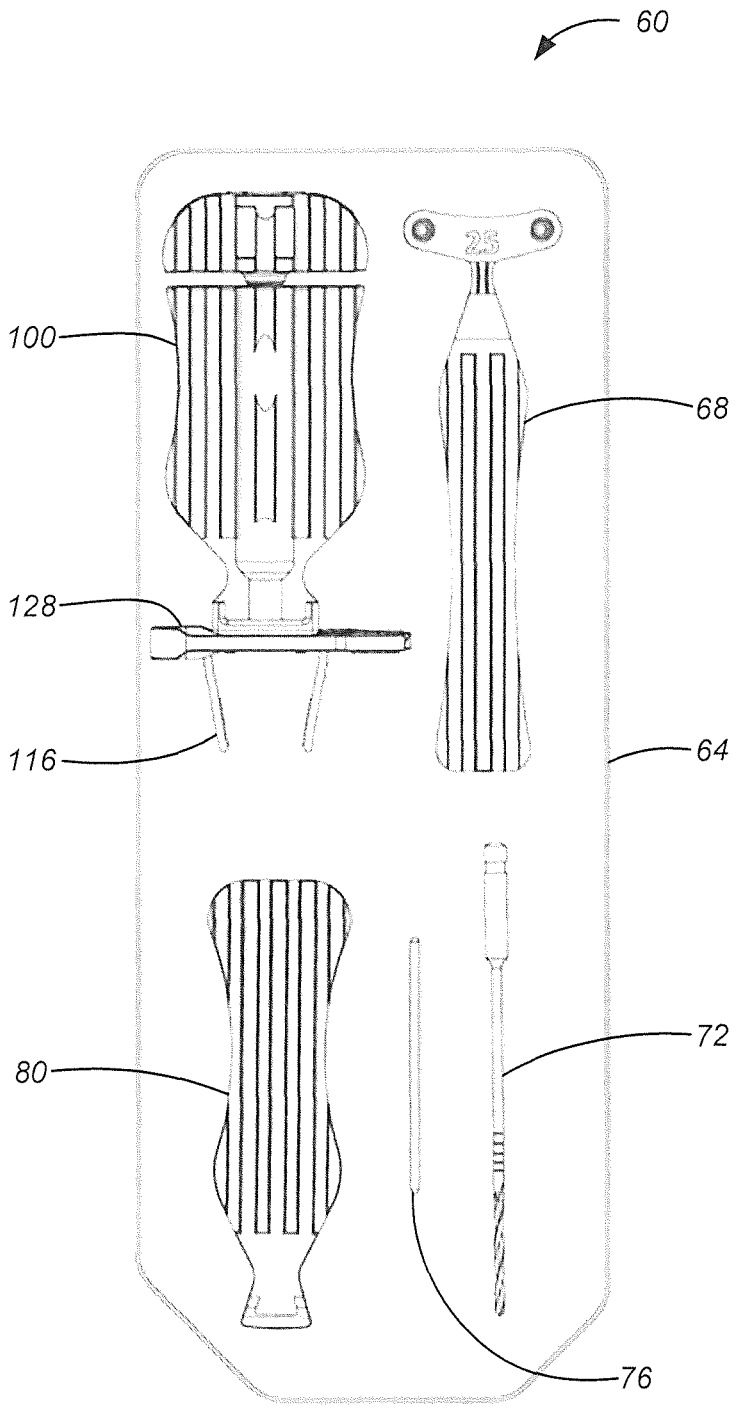
FIG. 1 illustrates a top plan view of an exemplary embodiment of a sterile staple implant kit in accordance with the present disclosure.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "first implant," may be made. However, the specific numeric reference should not be interpreted as a literal sequential order but rather interpreted that the "first implant" is different than a "second implant." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

In general, the present disclosure describes an apparatus and a method for a sterile staple implant kit that a surgeon may unpack and utilize during a surgery. The staple implant kit comprises a group of complementary surgery-specific instruments that are packaged in a sterile state. An instrument tray is configured to preserve the instruments in the sterile state until the staple implant kit is opened during the surgery. The instrument tray is configured to provide the surgeon with easy access to the instruments during the surgery. The staple implant kit comprises at least a staple inserter and a surgical staple suitable for being implanted in parallel holes drilled across a bone fusion or fixation site of a patient. In some embodiments, the staple implant kit may further comprise a bone drill, a drill guide, a locator pin, and a tamp. The surgical staple preferably is loaded in a relaxed configuration into the staple inserter. A staple retention clip is configured to retain the surgical staple coupled with the staple inserter until the staple is distracted during the surgery. A staple sizer is provided for determining sizes of surgical staples during the surgery.

FIG. 1 illustrates an exemplary embodiment of a sterile staple implant kit 60, in accordance with the present disclosure. The sterile staple implant kit 60 comprises a group of complementary surgical instruments that are sterilized and packaged together such that a surgeon may unpack and utilize the instruments during a bone fusion surgery. In the embodiment illustrated in FIG. 1, the instruments are supported in an instrument tray 64 that is configured to preserve the instruments in a sterile and undamaged state until the staple implant kit 60 is opened by the surgeon during surgery. Further, the instrument tray 64 provides the surgeon with easy access to the instruments during the surgery. In the embodiment of FIG. 1, the staple implant kit 60 comprises a drill guide 68, a bone drill 72, a locator pin 76, a tamp 80, and a staple inserter 100. In other embodiments, however, the staple implant kit 60 may comprise other surgical tools and components, such as by way of non-limiting example, drill guides, drill sizers, tamps, forceps, staple removal tools, drills, temporary pins, drill depth stops, fusion bone plates, bone plate fasteners, compression screws, and the like.

Figure 2A:
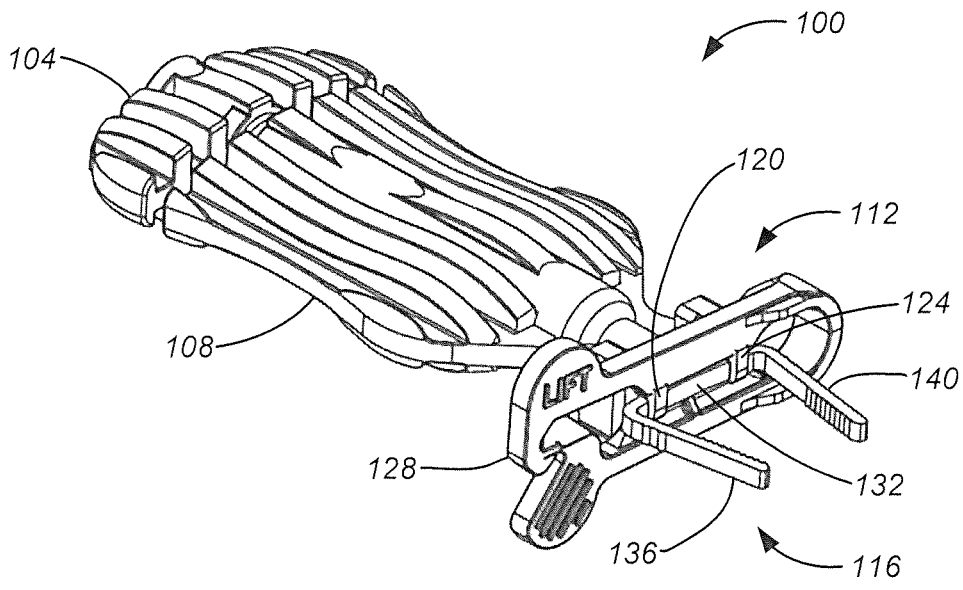
FIG. 2A illustrates a rearward upper perspective view of an exemplary embodiment of a staple inserter in accordance with the present disclosure.
Figure 2B:
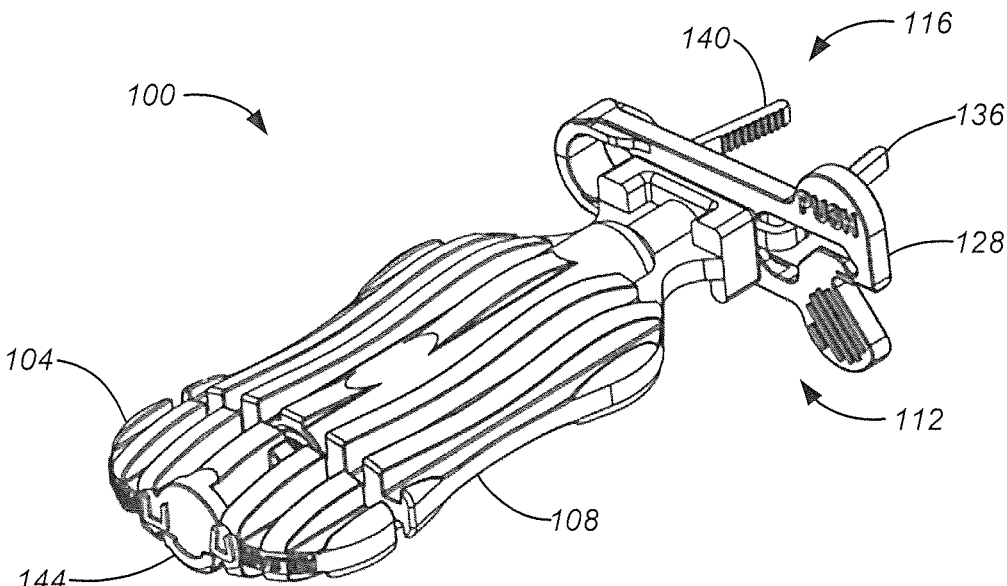
FIG. 2B illustrates a forward upper perspective view of the exemplary embodiment of the staple inserter illustrated in FIG. 2A, according to the present disclosure.

FIGS. 2A and 2B illustrate perspective views of an exemplary embodiment of the staple inserter 100 in accordance with the present disclosure. The staple inserter 100 comprises a proximal handle 104, a body 108, and a distal force applicator 112. In the embodiment illustrated in FIGS. 2A-2B, a surgical staple 116 is shown loaded within the distal force applicator 112, such that the surgical staple 116 is in a relaxed configuration suitable for packaging and shipping of the instrument 100 before being distracted during implantation of the surgical staple 116 at a bone fixation or fusion site of a patient. The surgical staple 116 generally is of a variety indicated for fixation of osteotomies and joint arthrodesis of the hands and feet. As such, the surgical staple 116 preferably is comprised of a metal alloy exhibiting shape memory and superelastic properties, such as Nitinol or other similar material. Further, in some embodiments, multiple teeth suitable for engaging with bone may be disposed on one or more exterior surfaces of the surgical staple 116, such as, for example, along a backspan or crown of the staple. In the embodiment illustrated herein, a multiplicity of teeth are disposed along each of a pair of legs of the surgical staple 116 so as to discourage movement of the staple once implanted in bone. It should be understood, however, that the staple inserter 100 is not to be limited to distracting surgical staples, but rather may be used in various other capacities, such as by way of non-limiting example, bending a bone fusion plate so as to tailor the plate to specific anatomy of a patient's bone being treated.

Figure 3A:
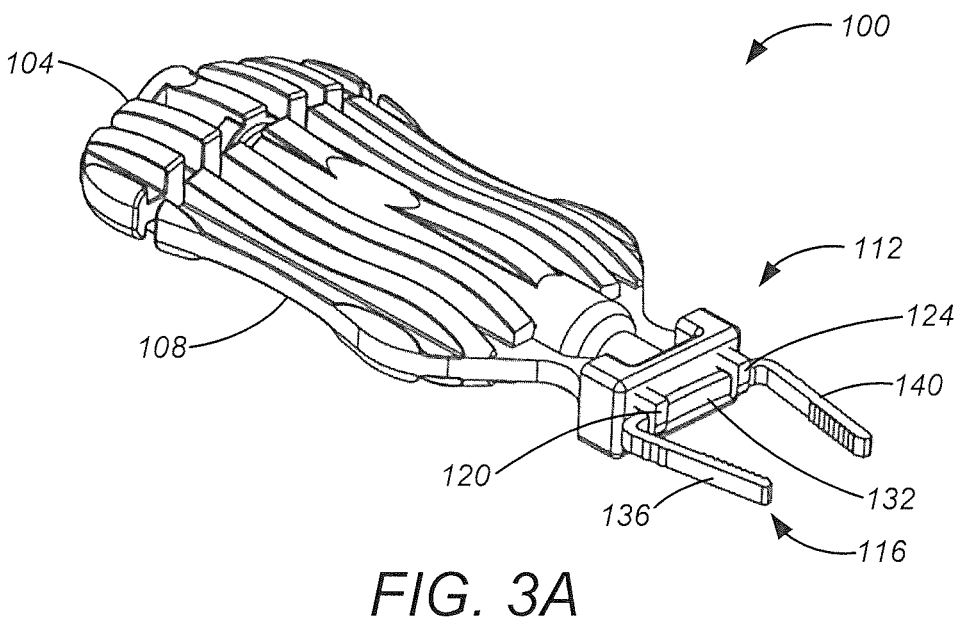
FIG. 3A illustrates a rearward upper perspective view of an exemplary embodiment of a staple inserter, according to the present disclosure.
Figure 3B:
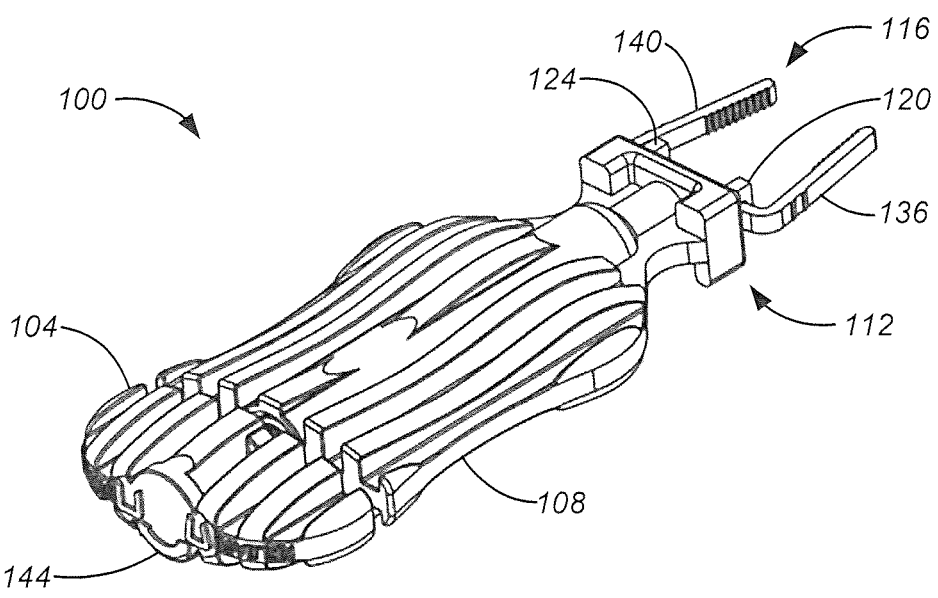
FIG. 3B illustrates a forward upper perspective view of the exemplary embodiment of the staple inserter illustrated in FIG. 3A, according to the present disclosure.

As best illustrated in FIGS. 3A-3B, the distal force applicator 112 comprises a first grip 120, a second grip 124, and a driver (not shown) centered there between. The first and second grips 120, 124 are configured to cooperate so as to support a crown 132 of the surgical staple 116 when the driver is placed into forcible contact with the center of the crown 132. The forces on the crown 132 due to the driver and the grips 120, 124 operate to retain the surgical staple 116 within the distal force applicator 112, thereby facilitating implanting the staple into the patient. As shown in FIG. 3A, the first and second grips 120, 124 engage the surgical staple 116 on the same side of the crown 132. A staple retention clip 128 prevents the crown 132 from becoming dislodged from the distal forced applicator 112 during packaging, sterilization, and shipping, as well as during distracting of the surgical staple 116, as described herein.

Preferably, the first and second grips 120, 124 have a separation distance comparable with the length of the crown 132. Thus, as illustrated in FIGS. 3A-3B, the first grip 120 is positioned near a first leg 136 of the surgical staple 132, and the second grip 124 is positioned near a second leg 140 of the staple. As will be appreciated, therefore, the distal force applicator 112 of the staple inserter 100 is configured to be used with specific sizes of surgical staples 116. In some embodiments, the staple inserter 100 may be configured with an overall size so as to be used with specific sizes of surgical staples 116. In some embodiments, a color-matching system may be utilized to indicate to the surgeon that certain surgical staples 116 may be implanted by way of the staple inserter 100. Further, in some embodiments, the first and second grips 120, 124 may have an adjustable separation distance so as to facilitate using the staple inserter 100 with a variety of differently-sized staples.

In the illustrated embodiment, the proximal handle 104 is mechanically coupled with the driver by way of a shaft that extends through the body 108. At least a portion of the shaft may comprise a threaded portion that rotatably engages with similar threads within a hole extending longitudinally through the body 108. In some embodiments, the driver may comprise a distal extension of the shaft, having a narrower diameter than proximal portions of the shaft. In some embodiments, the driver and the shaft may be separate components that are engaged with one another. The shaft generally is fixedly coupled with the proximal handle 104 such that rotating the proximal handle 104 relative to the body 108 rotates the shaft within the body 108, and thus moves the driver longitudinally relative to the body and the crown 132. Further, the proximal handle 104 may comprise a directional indicator 144 that indicates to the surgeon directions to rotate the proximal handle to distract and relax the surgical staple 116. In the illustrated embodiment, rotating the proximal handle 104 clockwise, as viewed from the perspective of a surgeon operating the instrument 100, distracts the surgical staple 116, and rotating the proximal handle counterclockwise relaxes the surgical staple.

When the driver is not in contact with the crown 132, or the contact is minimal, the surgical staple 116 is in an initial, relaxed configuration wherein the first leg 136 and the second leg 140 of the staple bend toward one another. The staple retention clip 128 serves to keep the crown 132 fixedly engaged with the grips 120, 124, as shown in FIGS. 2A-2B. As shown in FIG. 1, the staple inserter 100 preferably is stored in the staple implant kit 60 with the surgical staple 116 in the relaxed configuration and engaged with the grips 120, 124 by way of the staple retention clip 128. Thus, the staple implant kit 60 removes the burden, on the surgeon, of locating and loading a suitably sized staple onto an appropriate bending instrument, thereby allowing the surgeon to focus attention on other important aspects of the surgery.

During operation of the staple inserter 100, twisting the proximal handle 104 clockwise, as disclosed above, advances the shaft and moves the driver distally toward the crown 132. Once the driver contacts the center of the crown 132, the surgical staple 116 becomes clasped between the grips 120, 124 and the driver, at which point the staple retention clip 128 may be removed from the distal force applicator 112. Further clockwise twisting of the proximal handle 104 exerts an increasing degree of force onto the crown 132 by the grips 120, 124 and the driver. As will be appreciated, the distally-directed force due to the driver and proximally-directed forces due to the grips 120, 124 cause a corresponding distraction of the first and second legs 136, 140. Thus, clockwise twisting of the proximal handle 104 enables the surgeon to change the surgical staple 116 from the initial, relaxed configuration, shown in FIGS. 2A-2B, to a distracted configuration wherein the first and second legs 136, 140 are forced into a parallel relationship suitable for implanting the surgical staple 116 into a patient.

Once the surgical staple 116 is in the distracted configuration, and the staple retention clip 128 has been removed, the surgeon may use the staple inserter 100 to slide the first and second legs 136, 140 into parallel holes drilled across a bone fusion or fixation site of the patient. It will be appreciated that the forces exerted onto the crown 132 by the grips 120, 124 and the driver maintain the distracted configuration of the surgical staple 116 during implantation. The surgeon may insert the first and second legs 136, 140 into the parallel holes until the first and second grips 120, 124 come into contact with the patient's bone. The surgeon may then twist the proximal handle 104 counterclockwise so as to retract the driver proximally away from the crown 132, thereby allowing the surgical staple 116 to relax from the distracted configuration. The shape memory and superelastic properties of the material comprising the surgical staple 116 ensure that the staple advantageously compresses the bones to be fused as the staple attempts to return to the initial configuration illustrated in FIGS. 3A-3B. Once the driver has been suitably retracted from the crown 132, the surgeon may disengage the first and second grips 120, 124 from the crown and then use the tamp 80 to push the legs 136, 140 into the parallel holes until the crown 132 is in direct contact with the bone. The surgeon may then close the incision by way of suturing.

As disclosed with respect to FIG. 1, the staple implant kit 60 preferably comprises other surgical instruments that may assist the surgeon with using the staple inserter 100 and the surgical staple 116. In the illustrated embodiment, the staple inserter 100 and the surgical staple 116 are accompanied by the drill guide 68, the bone drill 72, the locator pin 76, and the tamp 80. In other embodiments, however, additional surgical instruments may be included in the staple implant kit 60, such as, by way of non-limiting example, drill sizers, forceps, staple removal tools, drill depth stops, fusion bone plates, bone plate fasteners, compression screws, and the like.

Figure 4:
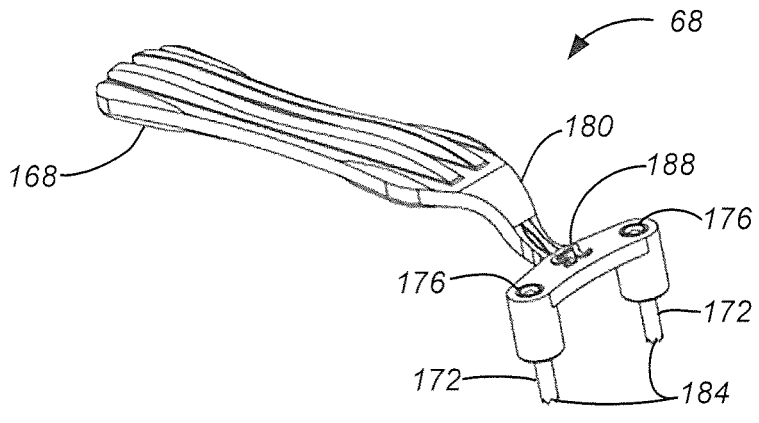
FIG. 4 illustrates an upper perspective view of an exemplary embodiment of a bone drill guide, according to the present disclosure.

FIG. 4 is a perspective view illustrating an exemplary embodiment of the drill guide 68 that may be included in the staple implant kit 60, according to the present disclosure. The drill guide 68 is a generally elongate member comprising a proximal handle 168 and a pair of parallel sleeves 172 configured to assist the surgeon with drilling osteotomy holes across a bone fusion or fixation site of a patient. An opening 176 into each of the parallel sleeves 172 is configured to receive the bone drill 72 and guide the drill into the interior of the sleeve. An angled portion 180 of the drill guide 68 is configured to facilitate simultaneously grasping the proximal handle 168 and drilling the osteotomy holes by way of the parallel sleeves 172. Distal teeth 184 disposed on the parallel sleeves 172 are configured to grip the bone of the patient and reduce movement of the drill guide 68 relative to the bone during drilling the osteotomy holes.

In the embodiment illustrated in FIG. 4, the drill guide 68 comprises a size indicator 188 disposed between the openings 176. The size indicator 188 corresponds to the distance between the positions of osteotomy holes that may be drilled by way of the drill guide 68. As will be recognized, the drill guide 68 aides the surgeon with preparing optimally positioned osteotomy holes for receiving the first and second legs 136, 140 in the distracted state of the surgical staple 116. As such, the size indicator 188 readily conveys to the surgeon the size of the surgical staple 116 that may be inserted into osteotomy holes created with the drill guide 68. It should be understood, however, that as members of the staple implant kit 60, illustrated in FIG. 1, the surgical staple 116 and drill guide 68 included in the kit preferably share complementary sizes. Thus, the drill guide 68 included in the staple implant kit 60 has a size that advantageously aides the surgeon with implanting the particular surgical staple 116 that is included in the kit. Further, in some embodiments, the size indicator 188 may include additional size-related information, such as information about the diameter of the sleeves 172, sizes of compatible drills, depth of the sleeves, and the like.

Figure 5:
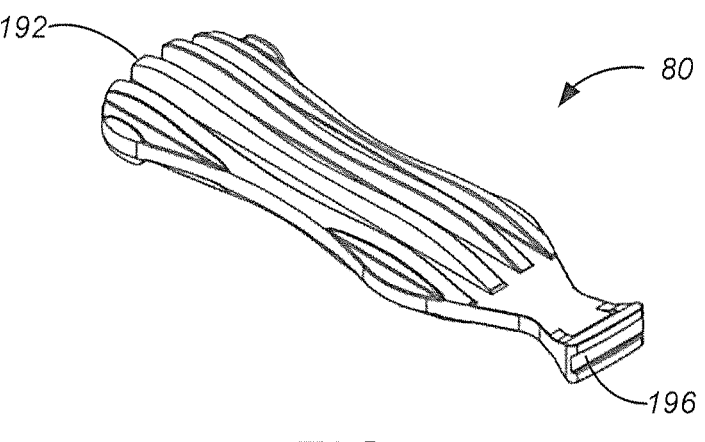
FIG. 5 illustrates a perspective view of an exemplary embodiment of a tamp in accordance with the present disclosure.

FIG. 5 is a perspective view illustrating an exemplary embodiment of the tamp 80 that may be included in the staple implant kit 60, in accordance with the present disclosure. The tamp 80 is a generally elongate member comprising a proximal handle 192 and a distal recess 196. As will be recognized, the tamp 80 advantageously enables the surgeon to push the legs 136, 140 into parallel osteotomy holes until the crown 132 is in direct contact with the bone of the patient. To this end, the distal recess 196 comprises a depth and a width configured to receive substantially an entirety of the crown 132. The proximal handle 192 is configured for grasping the tamp 80 during pushing of the crown 132 by way of the distal recess 196. In some embodiments, the tamp 80 may include a size indicator configured to display one or more sizes of the surgical staple 116 for which the tamp 80 is best suited.

Figure 6:
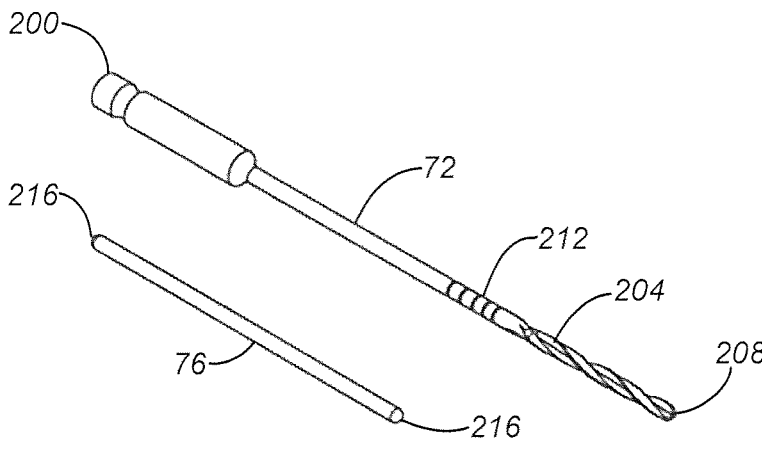
FIG. 6 illustrates an upper perspective view of an exemplary embodiment of a bone drill and a locator pin in accordance with the present disclosure.
Figure 7A:
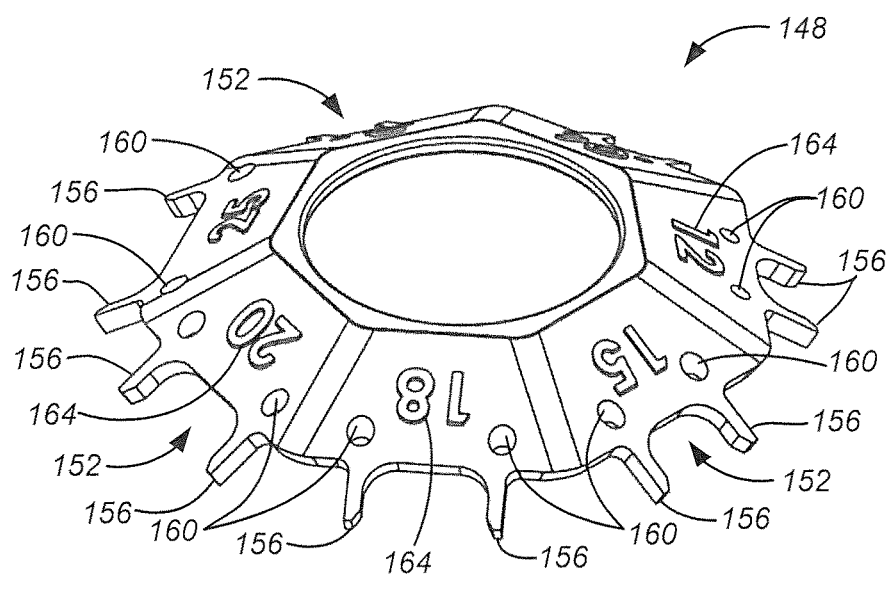
FIG. 7A illustrates a perspective view of an exemplary embodiment of a staple sizer, according to the present disclosure.
Figure 7B:
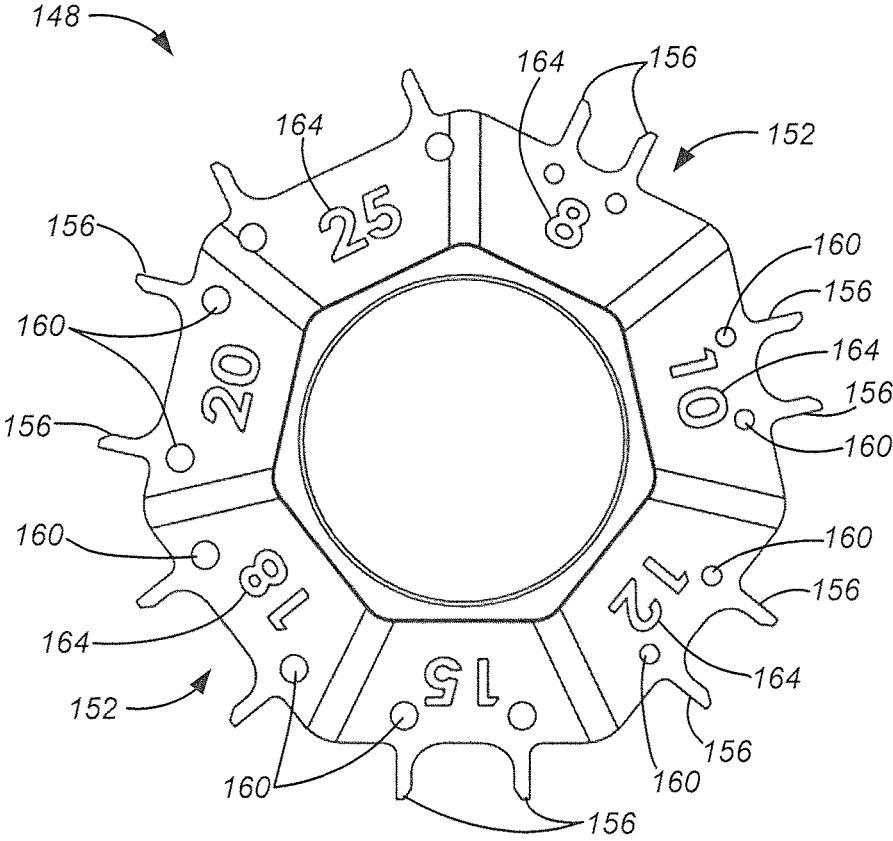
FIG. 7B illustrates a top plan view of the exemplary embodiment of the staple sizer illustrated in FIG. 7A in accordance with the present disclosure.
Figure 7C:
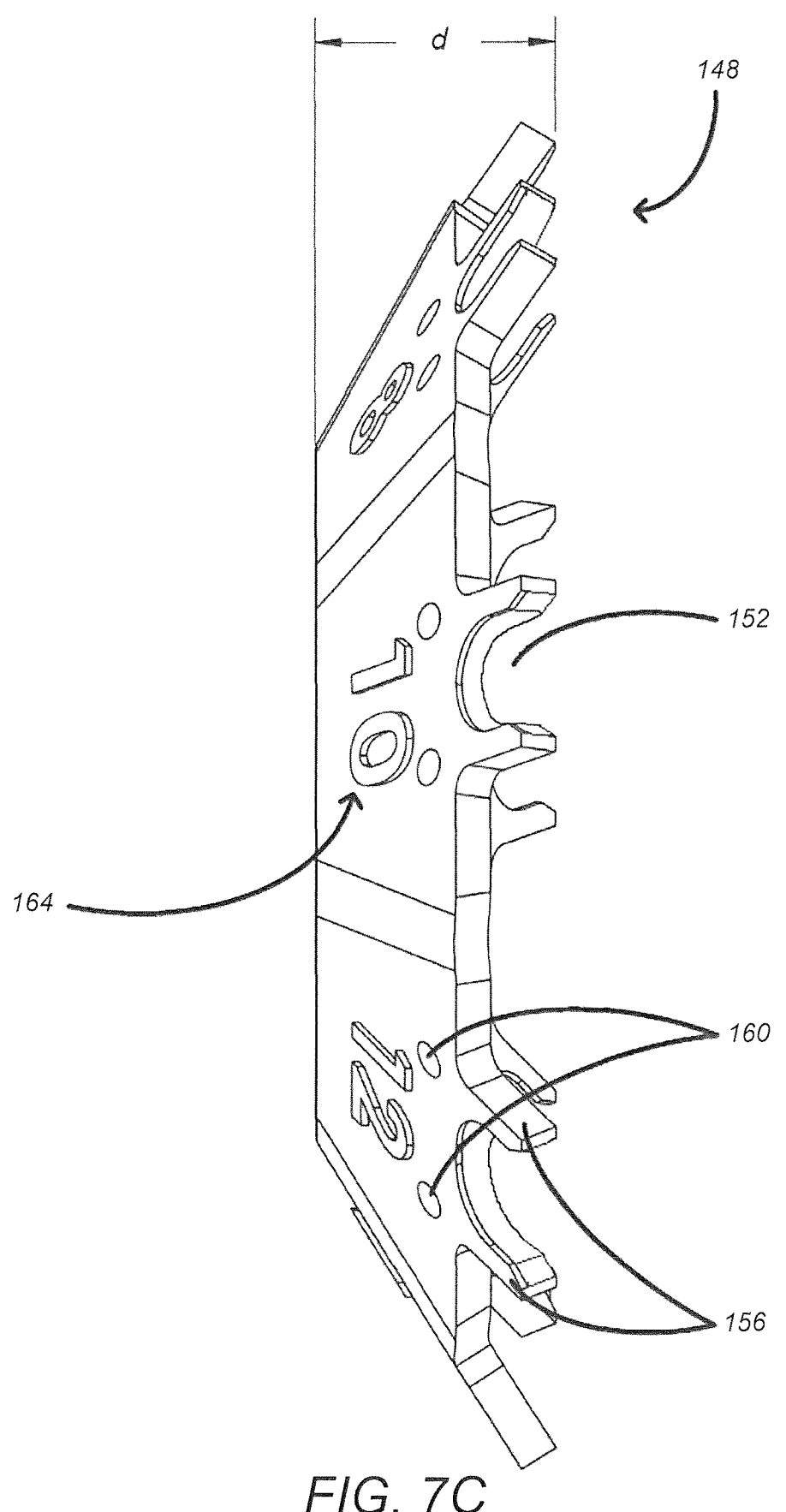
FIG. 7C illustrates a side plan view of the exemplary embodiment of the staple sizer illustrated in FIG. 7A in accordance with the present disclosure.
Figure 7D:
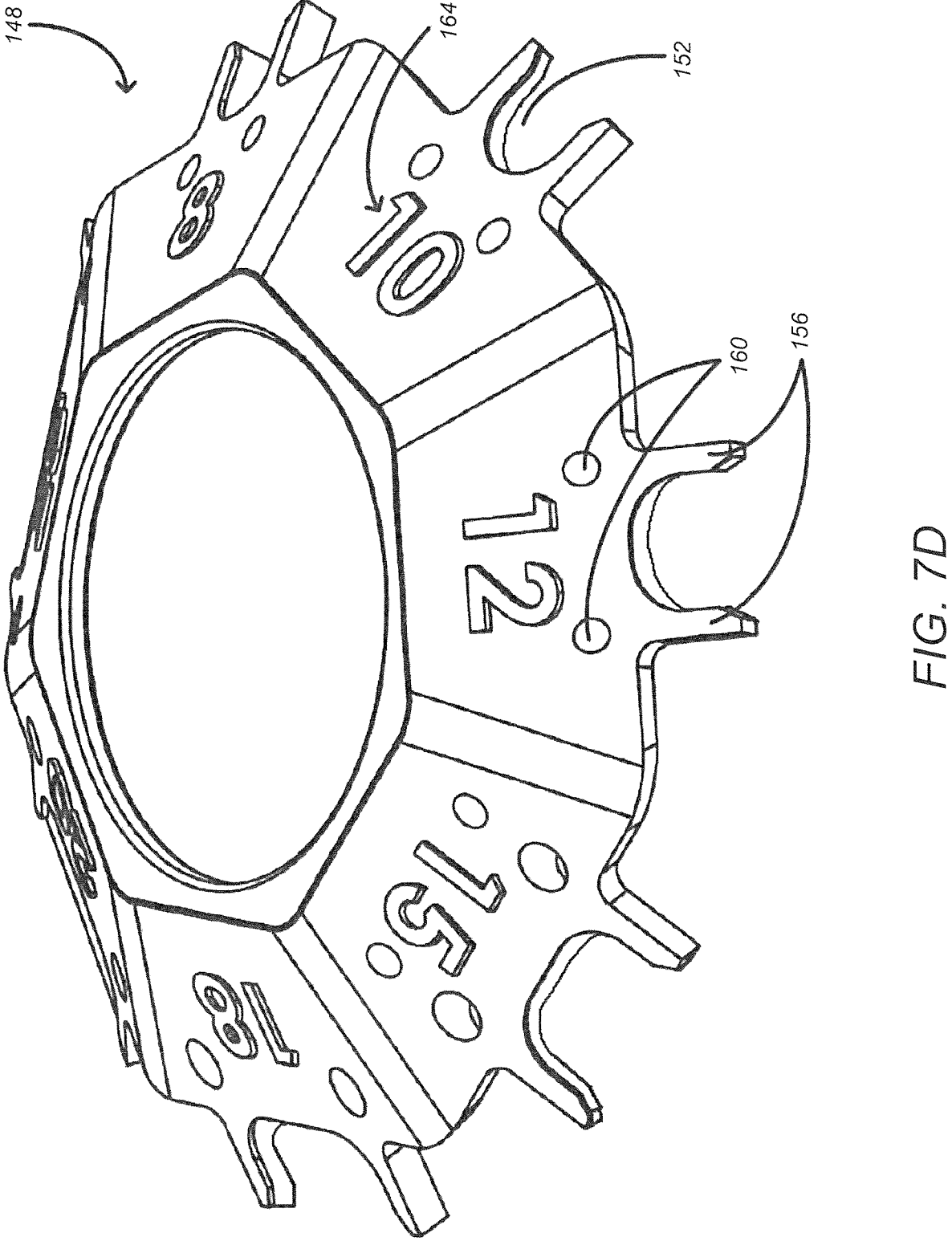
FIG. 7D illustrates a perspective view of an exemplary embodiment of the staple sizer illustrated in FIG. 7A, in accordance with the present disclosure.

FIG. 6 is a perspective view illustrating an exemplary embodiment of the bone drill 72 and locator pin 76 that may be included in the staple implant kit 60, according to the present disclosure. The bone drill 72 is a generally elongate member configured for drilling holes in human bone. The bone drill 72 comprises a proximal shank 200 configured to be received into a drill chuck. One or more flutes 204 angulate around a circumference of the drill and they extend to a distal cutting edge 208. As will be appreciated, the one or more flutes 204 are configured to transport bone cuttings away from the distal cutting edge 208 during drilling into bone. One or more depth annuli 212 may be disposed proximal to the flutes 204. Preferably, the depth annuli 212 may assist the surgeon with drilling osteotomy holes to a desired depth.

The locator pin 76 generally comprises a small, symmetric shaft comprising rounded ends 216 and a diameter suitable to be received into the sleeves 172 of the drill guide 68. It is envisioned that the locator pin 76 and the bone drill 72 may be used in conjunction with the drill guide 68 to drill parallel osteotomy holes across a bone fusion or fixation site of a patient. For example, during a bone fusion surgery, the surgeon may hold the drill guide 68 such that the sleeves 172 are centered across the bone fusion or fixation site and then insert the bone drill 72 into a first of either of the sleeves 172 to drill a first osteotomy hole into the bone of the patient. Upon removing the bone drill 72, the surgeon may insert the locator pin 76 through the sleeve 172 and into the newly drilled first osteotomy hole. With the locator pin 76 positioned in the first sleeve 172 and the first osteotomy hole, the surgeon may insert the bone drill 72 into a second sleeve 172 and drill a second osteotomy hole. It should be understood, therefore, that the locator pin 76, the bone drill 72, and the drill guide 68 advantageously enable the surgeon to drill osteotomy holes that are optimally positioned to receive the first and second legs 136, 140 in the distracted state of the surgical staple 116, as disclosed herein.

As will be recognized, some surgical procedures may necessitate removing a surgical staple, such as the surgical staple 116, from a bone fusion or fixation site of a patient. It is envisioned that the surgeon may lift the crown 132 away from the patient's bone surface by way of a suitable removal tool so as to create enough clearance for the surgeon to engage the grips 120, 124 between the bone and the crown 132. With the first and second grips 120, 124 suitably engaged with the crown 132, the surgeon may turn the proximal handle 104 clockwise to distally advance the driver into contact with the center of the crown 132. Upon twisting the proximal handle 104 so as to place the surgical staple 116 into the distracted configuration, the surgeon may use the staple inserter 100 to pull the first and second legs 136, 140 free of the patient's bone.

It should be understood that although the instruments comprising the staple implant kit 60 have been discussed in combination with the surgical staple 116, the staple implant kit 60 is not to be limited to implanting surgical staples. Rather, the instruments comprising the staple implant kit 60 may be used in various capacities other than as described herein, such as, by way of non-limiting example, bending a bone fusion plate so as to tailor the plate to a specific anatomy of a patient's bone being treated. Accordingly, the instruments comprising the staple implant kit 60 preferably are comprised of rigid materials suitable for bending surgical implants, such as surgical staples and bone fusion plates, as described herein. In some embodiments, the rigid materials may be comprised of metal, plastic, or a combination of the two.

As disclosed above, the staple inserter 100 may be configured for use with specific sizes of surgical staples 116. To this end, one or more staple inserters 100 may be used in conjunction with a staple sizer 148, as shown in FIGS. 7A-7D. The staple sizer 148 is a generally disc-shaped member comprising a plurality of sections 152 corresponding to different sizes of surgical staples, such as the surgical staple 116. Each of the plurality of sections 152 comprises a pair of parallel protrusions 156 extending away from the center of the stable sizer 148 and disposed adjacently to a pair of holes 160. The parallel protrusions 156 correspond to the positions of the first and second legs 136, 140 in the distracted state of the surgical staple 116. The pair of holes 160 indicate the relationship between osteotomy holes suitably drilled across a bone fusion or fixation site of the patient. Each section 152 comprises a size indicator 164 that displays a size of the surgical stable 116 that, when distracted, comprises first and second legs 136, 140 that substantially match the positions of the parallel protrusions 156. Further, the first and second legs 136, 140 of a distracted surgical staple 116 may be inserted through the pair of holes 160 in an appropriate section 152 without effort.

As disclosed above, it is envisioned that the staple sizer 148 may be utilized during osteotomy to assist the surgeon in selecting an appropriately sized surgical staple 116. For example, after drilling osteotomy holes across a bone fixation site of the patient, the surgeon may compare the osteotomy holes with the parallel protrusions 156 of the staple sizer 148. Upon finding a pair of the parallel protrusions 156 that best match the osteotomy holes, the surgeon may refer to the size indicator 164 to determine an appropriately sized surgical staple 116 for implantation into the osteotomy holes of the patient. The surgeon may compare the first and second legs 136, 140 of the distracted surgical staple 116 with the holes 160 to verify the suitability of the staple for implantation into the patient. As will be appreciated, the staple sizer 148 effectively enables the surgeon to select an appropriately sized surgical staple 116, as well as the associated staple inserter 100, without being forced to unpack multiple unneeded staple implant kits 60 in an attempt to locate a desired size of the staple.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A sterile staple implant kit, comprising:
a surgical staple for fixating osteotomies;
a staple inserter for implanting the surgical staple wherein the staple inserter comprises a first grip, a second grip, a driver, and a body supporting a distal force applicator configured to hold the surgical staple;
a staple retention clip coupled to retain the surgical staple to the distal force applicator; the staple retention clip configured to be removed from the distal force applicator during or after distracting the surgical staple prior to being implanted into a bone of a patient;
the staple loaded into the staple inserter in the relaxed configuration before being distracted during implantation at a bone fixation or fusion site of a patient; and
a group of complementary instruments packaged in a sterile state.

2. The sterile staple implant kit of claim 1, further comprising an instrument tray configured to preserve the instruments in the sterile state and provide easy access to the instruments during the surgery.

3. The sterile staple implant kit of claim 1, wherein the surgical staple is loaded into the staple inserter in a relaxed configuration of the surgical staple.

4. The sterile staple implant kit of claim 1, wherein the group of instruments includes any one or more of the staple inserter, the surgical staple, a bone drill, a drill guide, a locator pin, and a tamp.

5. The sterile staple implant kit of claim 4, wherein the group of instruments includes any one or more of a drill sizer, forceps, a staple removal tool, a drill depth stop, a fusion bone plate, bone plate fasteners, compression screws, or any combination thereof.

6. The sterile staple implant kit of claim 4, wherein the drill guide is configured to guide directly drilling parallel holes across a bone fusion or fixation site of a patient.

7. The sterile staple implant kit of claim 6, wherein the drill guide includes a first sleeve and a second sleeve that respectively correspond to a first leg and a second leg of the surgical staple in a distracted configuration.

8. The sterile staple implant kit of claim 7, wherein the first sleeve and the second sleeve are configured to guide a bone drill during drilling the parallel holes.

9. The sterile staple implant kit of claim 1, wherein the staple inserter comprises a body supporting a distal force applicator that is mechanically coupled with a proximal handle.

10. The sterile staple implant kit of claim 9, wherein the distal force applicator is configured to distract the surgical staple when the proximal handle is rotated in a clockwise direction.

11. The sterile staple implant kit of claim 10, wherein the distal force applicator includes a driver that moves relative to a crown of the surgical staple when the proximal handle rotates.

12. The sterile staple implant kit of claim 11, wherein the proximal handle is mechanically coupled with the driver by way of a shaft that extends through the body.

13. The sterile staple implant kit of claim 12, wherein the shaft includes a threaded portion that rotatably engages with threads disposed within a hole extending through the body.

14. The sterile staple implant kit of claim 11, wherein the driver comprises a distal extension of the shaft and has a narrower diameter than proximal portions of the shaft.

15. The sterile staple implant kit of claim 14, wherein the driver and the shaft are separate components that are engaged with one another.

16. The sterile staple implant kit of claim 14, wherein the proximal handle includes an indicator that shows directions to rotate the proximal handle to distract and relax the surgical staple.

17. The sterile staple implant kit of claim 16, wherein the indicator shows that rotating the proximal handle in a counterclockwise direction relaxes the surgical staple.

18. The sterile staple implant kit of claim 16, wherein the indicator shows that rotating the proximal handle in a clockwise direction distracts the surgical staple.

19. The sterile staple implant kit of claim 18, wherein clockwise rotation of the proximal handle clasps the surgical staple between the driver and a first grip and a second grip disposed near the distal force applicator.

\* \* \* \* \*